(12) United States Patent
Shiozawa et al.

(10) Patent No.: US 10,242,838 B2
(45) Date of Patent: Mar. 26, 2019

(54) X-RAY GENERATING UNIT AND RADIOGRAPHIC APPARATUS

(71) Applicant: CANON KABUSHIKI KAISHA, Tokyo (JP)

(72) Inventors: Takashi Shiozawa, Tokyo (JP); Kazuyuki Ueda, Tokyo (JP); Kazuya Tsujino, Tokyo (JP); Nobuhiro Ito, Yamato (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 138 days.

(21) Appl. No.: 15/039,814

(22) PCT Filed: Sep. 11, 2014

(86) PCT No.: PCT/JP2014/074758
§ 371 (c)(1),
(2) Date: May 26, 2016

(87) PCT Pub. No.: WO2015/079783
PCT Pub. Date: Jun. 4, 2015

(65) Prior Publication Data
US 2016/0379794 A1    Dec. 29, 2016

(30) Foreign Application Priority Data

Nov. 29, 2013 (JP) ................ 2013-247132

(51) Int. Cl.
*A61B 6/00* (2006.01)
*G21K 1/02* (2006.01)
*H01J 35/08* (2006.01)

(52) U.S. Cl.
CPC ............... *H01J 35/08* (2013.01); *G21K 1/02* (2013.01); *A61B 6/502* (2013.01); *H01J 2235/087* (2013.01); *H01J 2235/166* (2013.01)

(58) Field of Classification Search
CPC ......... A61B 6/025; A61B 6/107; A61B 6/405; A61B 6/0414; A61B 6/4007; A61B 6/42; A61B 6/502; H01J 2235/068; H01J 2235/087; H01J 35/06; H01J 35/08; H01J 35/16
See application file for complete search history.

(56) References Cited

U.S. PATENT DOCUMENTS 6,370,218 B1 * 4/2002 Toth ................. A61B 6/032
378/113
2009/0022264 A1    1/2009 Zhou
(Continued)

FOREIGN PATENT DOCUMENTS

CN    101395691 A    3/2009
CN    102209494 A    10/2011
(Continued)

*Primary Examiner* — Chih-Cheng Kao
(74) *Attorney, Agent, or Firm* — Canon USA, Inc., IP Division

(57) ABSTRACT

A radiographic apparatus including a target array and an X-ray detecting unit. The target array includes a plurality of targets and a forward shielding member. The forward shielding member includes a plurality of partitions. The X-ray detecting unit includes a detecting portion. The partitions each have sloping surfaces whose angles of inclination change along an array direction.

22 Claims, 10 Drawing Sheets

(56) References Cited

U.S. PATENT DOCUMENTS

| | | | |
|---|---|---|---|
| 2009/0232270 A1* | 9/2009 | Okunuki | A61B 6/00 378/5 |
| 2009/0232272 A1 | 9/2009 | Tsujii | |
| 2014/0241492 A1* | 8/2014 | Tamura | A61B 6/025 378/22 |

FOREIGN PATENT DOCUMENTS

| JP | S6483139 A | 3/1989 |
|---|---|---|
| JP | H01204649 A | 8/1989 |
| JP | 2001037746 A | 2/2001 |
| JP | 2003114203 A | 4/2003 |
| JP | 2009205992 A | 9/2009 |
| JP | 2011-081930 A | 4/2011 |
| JP | 2012033505 A | 2/2012 |
| JP | 2012175997 A | 9/2012 |

\* cited by examiner

X-RAY GENERATING UNIT AND RADIOGRAPHIC APPARATUS

TECHNICAL FIELD

The present invention relates to a radiographic apparatus used in the field of medical equipment. In particular, the present invention relates to a radiographic apparatus including an X-ray generating unit, the X-ray generating unit including a plurality of targets and a forward shielding member.

BACKGROUND ART

In the field of recent radiography such as mammography, tomosynthesis imaging has come to be employed as a method of separating information on an object in the depth direction of the object. In tomosynthesis imaging, a plurality of images are acquired by applying X-rays to an object from a plurality of angles, and the plurality of images thus acquired are reconstructed into a tomographic image.

There is a tomosynthesis imaging technique in which X-rays are applied to an object from a plurality of angles by sequentially using a plurality of X-ray sources that are held stationary. U.S. Patent Application Publication No. 2004/0213378 discloses a radiographic apparatus that includes an X-ray source unit in which a plurality of X-ray sources are arrayed at predetermined intervals, and a shielding member unit having a plurality of apertures provided in correspondence with the X-ray sources that are arrayed.

SUMMARY OF INVENTION

Technical Problem

One of major factors that determine the resolution of an image acquired by a radiographic apparatus is the focal spot diameter of the X-ray source. In each embodiment of the present invention, the size of focal spots of the radiographic apparatus substantially corresponds to the size of focal spots of electron beams emitted from electron sources to the respective targets. Hereinafter, the focal spot of an electron beam that is defined on a target is referred to as "focal spot."

From the viewpoint of increasing the resolution of an image to be acquired, the focal spot diameter is desired to be as small as possible. On the other hand, from the viewpoints of the heat resistance of a material forming the target and the intensity of the X-rays, the upper limit of the density of the anode current flowing through the target and the lower limit of the focal spot diameter are set forth. In general, a finite "focal spot diameter" is employed with a lower limit of several dozens of microns in view of heat resistance of the target and with an upper limit of several millimeters in view of resolution.

In the radiographic apparatus disclosed by U.S. Patent Application Publication No. 2004/0213378, the shielding member unit having the plurality of apertures that are provided in correspondence with the array of X-ray sources included in the X-ray source unit is provided on the front side of the X-ray source unit.

The shielding member unit includes "partitions" so that the plurality of X-ray beams can be extracted separately from one another in the form of an array. The partitions have a "height (thickness)" for attenuating the X-rays so as to prevent the emission of X-rays in undesired directions. In general, the "height" of the partitions included in the shielding member unit ranges from 0.1 mm or larger to several dozens of millimeters or smaller in a direction from the focal spots toward an X-ray detecting unit.

In the radiographic apparatus including such a shielding member unit, penumbras attributed to the "focal spot diameter" and the "height" of the partitions of the shielding member unit are inevitably formed on the outer sides of each X-ray beam in a direction in which the plurality of targets are arrayed. A penumbra is an X-ray component whose intensity in a focal image seen from a detector is lower than that of a main X-ray component. The penumbra is an unnecessary component that may cause an artifact in the acquired image. Moreover, the intensity of X-rays forming the penumbra changes in the direction in which the plurality of targets are arrayed. Therefore, the penumbra is an unnecessary component also in terms of triggering deterioration in the quality of the acquired image.

In a radiographic apparatus including a single target, penumbras can be reduced to an ignorable level by increasing the "height" of a forward shielding member. On the other hand, in a radiographic apparatus including a plurality of targets and a shielding member unit, a plurality of X-ray beams are made to coincide with one another. To do so, the "height" of the partitions is limited. Consequently, large penumbra regions are produced.

Moreover, since such penumbra regions are produced on the outer sides of a main exposed region, whose focal spot is not eclipsed, in the direction in which the plurality of targets are arrayed, the penumbra regions tend to leak to the outside of the radiographic apparatus rather than into the main exposed region.

To suppress the leakage of penumbras to the outside of the radiographic apparatus, the entirety of the radiographic apparatus may be covered with a shielding member. In such a configuration, however, the weight increases and the center of gravity is raised. Consequently, the radiographic apparatus becomes unstable, increasing the probability of image blurring during imaging. Hence, in terms of usability and imaging performance, there has been a demand for a radiographic apparatus in which the range of the penumbra is limited by an effective arrangement of shielding members.

In another proposal, the radiographic apparatus including the shielding member unit is applied to tomography in which imaging is performed by making the ranges of different X-ray beams coincide with one another. Japanese Patent Laid-Open No. 2010-115270 discloses an X-ray generating unit including a shielding member unit having a plurality of variable apertures that are provided in correspondence with a plurality of transmission-type targets. In Japanese Patent Laid-Open No. 2010-115270, a plurality of X-ray beams are made to coincide with one another by adjusting the positions of the variable apertures—provided in the shielding member unit, which is of a lattice type.

In a radiographic apparatus including such a shielding member unit, beams transmitted through corner portions of the shielding member unit produce penumbras. Penumbras are X-ray components that have been transmitted through the shielding member unit. There has been a need for reducing such penumbras because the penumbras may leak to the outside of the radiographic apparatus or the penumbras may cause artifacts in the resulting tomographic image.

The present invention provides a radiographic apparatus in which penumbras that may leak to the outside of the radiographic apparatus are reduced. The present invention also provides an X-ray generating unit in which penumbras attributed to the shape of a forward shielding member are reduced.

Solution to Problem

According to an aspect of the present invention, there is provided an X-ray generating unit including a plurality of targets that are arrayed in a line, a forward shielding member including a plurality of partitions that each separate adjacent ones of the targets, and an electron source that emits electron beams to electron incident surfaces of the plurality of targets, respectively. The partitions each have sloping surfaces each inclining with respect to a normal line that is normal to a corresponding one of the electron incident surfaces, and angles of inclination of the sloping surfaces with respect to the respective normal lines change with positions of the sloping surfaces along an array direction in which the targets are arrayed.

According to another aspect of the present invention, there is provided a radiographic apparatus including the above X-ray generating unit, and an X-ray detecting unit that includes a detecting portion facing the target array and including a plurality of detecting devices.

Further features of the present invention will become apparent from the following description of exemplary embodiments with reference to the attached drawings.

DESCRIPTION OF EMBODIMENTS

Embodiments of the present invention concerning an X-ray generating unit and a radiographic apparatus will now be described with reference to the attached drawings. The materials, dimensions, shapes, relative positions, and other factors of elements described in the following embodiments do not limit the scope of the present invention unless otherwise stated.

An X-ray generating unit according to a general embodiment of the present invention will first be described with reference to FIGS. 1A to 5D.

Figure 1A:
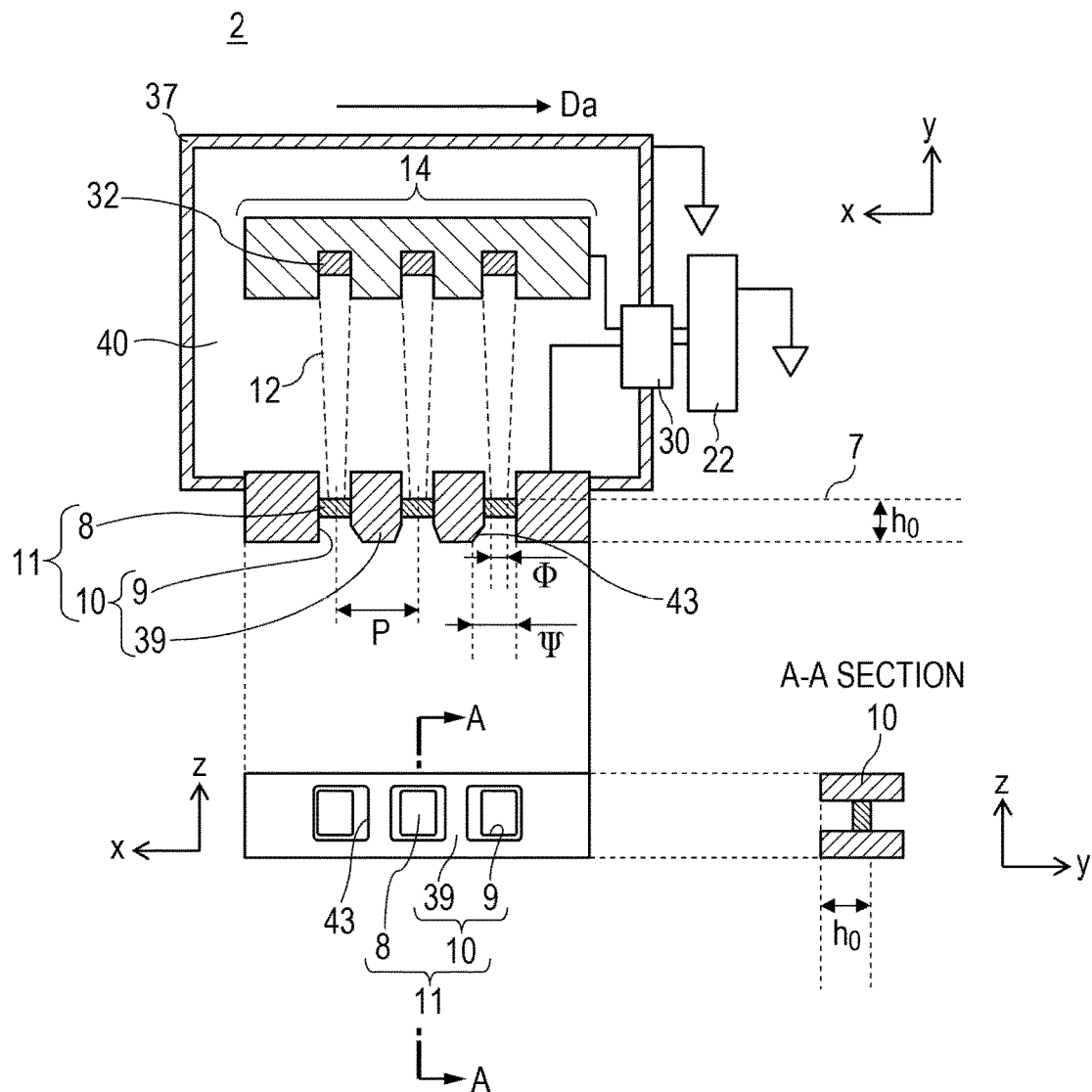
FIG. 1A is a three-way view of an X-ray generating unit according to a general embodiment of the present invention.
Figure 1B:
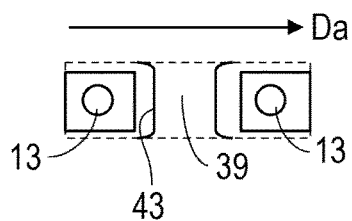
FIG. 1B is an enlarged view illustrating one of partitions.

An X-ray generating unit 2 according to the general embodiment of the present invention will be described with reference to FIGS. 1A, 1B, and 2. FIG. 1A is a three-way view of the X-ray generating unit 2 according to the general embodiment of the present invention. FIG. 1B is an enlarged view illustrating one of partitions 39 included in a forward shielding member 10.

As illustrated in FIG. 1A, the X-ray generating unit 2 according to the general embodiment includes a target array 11 and an electron source 14. The target array 11 includes a plurality of targets 8 that generate X-rays, and the forward shielding member 10. The electron source 14 includes a plurality of electron emitting portions 32.

As illustrated in FIGS. 1A and 1B, the plurality of targets 8 are each a transmission-type target having an electron incident surface 7 and an emitting surface that is opposite the electron incident surface 7. The targets 8 are arrayed in a line in a predetermined array direction Da.

As illustrated in FIGS. 1A and 1B, the forward shielding member 10 has a plurality of apertures 9 provided in correspondence with the plurality of targets 8. That is, the plurality of apertures 9 are arrayed in the array direction Da, as with the plurality of targets 8. The forward shielding member 10 further includes a plurality of partitions 39 that each separate adjacent ones of focal spots 13 from each other as illustrated in FIG. 1B. The partitions 39 each extend in a direction from the electron incident surfaces 7 toward the emitting surfaces of the targets 8. Each pair of partitions 39 are regarded as defining the aperture diameter of a corresponding one of the apertures 9 in the array direction Da.

As illustrated in FIG. 1A, the electron source 14 is configured such that electron beams 12 are applied to the electron incident surfaces 7 of the plurality of targets 8, respectively, whereby the focal spots 13 are formed. In such a configuration, referring now to FIG. 2, the X-ray generating unit 2 emits X-rays from the focal spots 13 such that a plurality of main exposed regions 38 that are separated from one another in the array direction Da by the partitions 39 are extracted from the plurality of apertures 9, respectively. In FIG. 2, the focal spots 13 formed on the respective electron incident surfaces 7 of the targets 8 are not illustrated.

The shapes of the partitions 39 and the apertures 9 in the array direction Da that characterize the X-ray generating unit 2 according to the general embodiment of the present invention will now be described with reference to FIG. 2.

Figure 2:
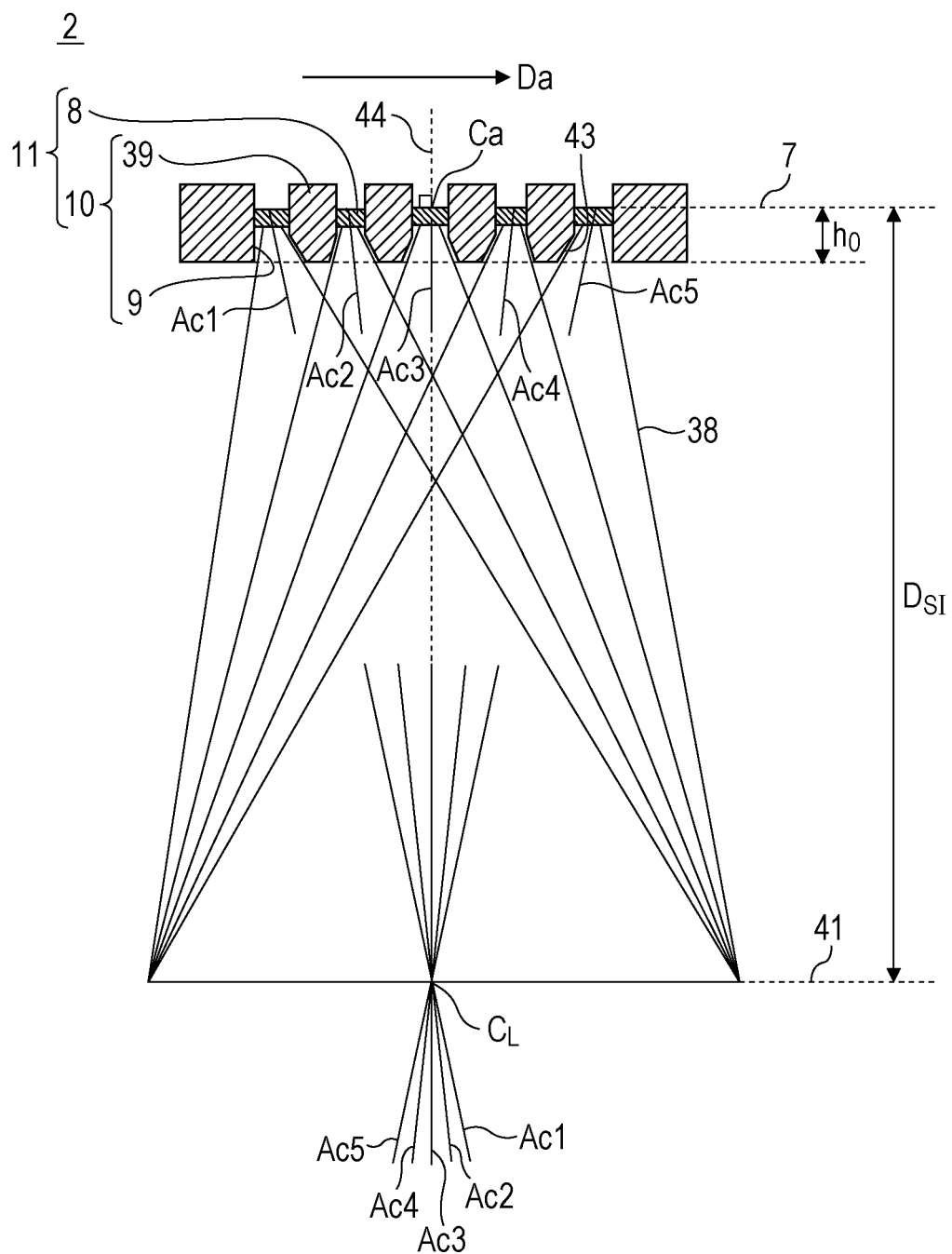
FIG. 2 is an enlarged view illustrating a target array included in the X-ray generating unit according to the general embodiment of the present invention and also illustrating how X-ray beams coincide with one another.

FIG. 2 illustrates an embodiment of the target array 11 in which a number n of targets 8 that are arrayed is five. As illustrated in FIG. 2, the plurality of partitions 39 each have sloping surfaces 43 that slope with respect to lines that are normal to the respective electron incident surfaces 7. The plurality of main exposed regions 38 emitted from the target array 11 coincide with one another on a detecting plane 41, which faces the forward shielding member 10, and in an area having a length Li. Among the lines that are normal to the electron incident surfaces 7 illustrated in FIG. 2, the central normal line 44 passing through an exposure center $C_L$, in the array direction Da, of the area in which the main exposed regions 38 coincide with one another is illustrated as a representative.

If the elements included in the target array 11 and the focal spots 13 are arranged symmetrically with respect to one of the lines normal to the electron incident surfaces 7 that passes through an array center Ca of the target array 11 as in the case illustrated in FIG. 2, the central normal line 44 passes through the array center Ca. If the elements included in the target array 11 or the focal spots 13 are arranged asymmetrically with respect to a normal line passing through the array center Ca, the central normal line 44 may not necessarily pass through the array center Ca and may pass through one of the partitions 39. Such a configuration is also within the scope of the present invention.

As illustrated in FIG. 2, in the target array 11 according to the general embodiment, the sloping surfaces 43 of the plurality of partitions 39 define center axes Ac1 to Ac5 of the respective apertures 9 in the array direction Da. Truncated pyramids are inscribed in the respective apertures 9, with surfaces of the targets 8 on which the focal spots 13 are defined being the upper surfaces of the respective truncated pyramids. The center axes Ac1 to Ac5 are each uniquely defined in a corresponding one of the truncated pyramids as a straight line connecting the center of a corresponding one of the focal spots 13 and the center of a corresponding one of aperture planes at the apertures 9. The aperture planes of the apertures 9 are each uniquely defined as an open portion produced by virtually cutting the forward shielding member 10 along a virtual plane extending at a height $h_0$ from a corresponding one of the electron incident surfaces 7.

With the X-ray generating unit 2 according to the general embodiment including at least the plurality of targets 8 and the forward shielding member 10 having the apertures 9 provided in correspondence with the targets 8, the problem of vibrations that may occur with the rotational movement of the known X-ray generating unit is avoided. Hence, the X-ray generating unit 2 according to the general embodiment does not have the problem of image blurring caused by vibrations that may occur in the known X-ray generating unit with the rotational movement of the X-ray generating unit.

In the general embodiment, the partitions 39 each have the sloping surfaces 43, and the angle of inclination of each of the sloping surfaces 43 with respect to the central normal line 44 is changed with the position thereof in the array direction Da. Thus, penumbra regions 45 attributed to the partitions 39 of the forward shielding member 10 are reduced. Consequently, in the X-ray generating unit 2 according to the general embodiment, undesired leakage of the X-rays around the X-ray generating unit 2 is reduced.

A problem of attenuation-attributed penumbras that is to be solved in the present invention will now be described with reference to FIG. 3.

Figure 3:
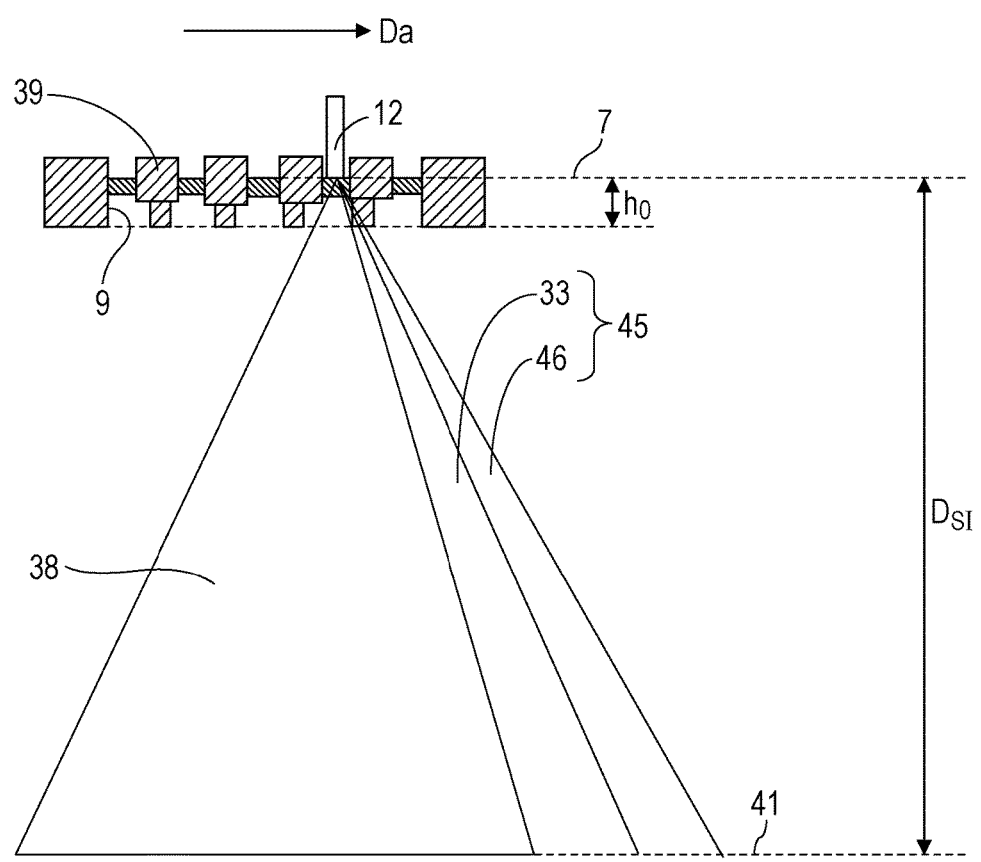
FIG. 3 is an enlarged view illustrating a known target array including partitions having no sloping surfaces.

FIG. 3 is an enlarged view illustrating a known exemplary target array including partitions 39 having no sloping surfaces. The known example corresponds to an embodiment illustrated in FIG. 2(a) of Japanese Patent Laid-Open No. 2010-115270. In the known example, shielding members are provided on the partitions 39 at respective positions that differ with the positions of a plurality of apertures 9 and such that a plurality of main exposed regions 38 extracted from the respective apertures 9 coincide with one another. Consequently, in the known example, each of the partitions 39 has a step such that each of the apertures 9 has a stepped portion in the array direction Da. A shape of each of the main exposed regions 38 in the array direction Da is defined by a corresponding one of the apertures 9 that each have the stepped portion.

As illustrated in FIG. 3, a penumbra region 45 is formed on an outer side of the main exposed region 38 in the array direction Da. The penumbra region 45 includes an eclipse-attributed penumbra region 33 attributed to a partial eclipse of the X-ray beam, forming a focal spot image, by a corresponding one of the partitions 39, and an attenuation-attributed penumbra region 46 attributed to the attenuation of the X-ray beam that is caused by a portion of the X-ray beam that has been transmitted through a thin portion of the partition 39. The attenuation-attributed penumbra region 46 is formed on the outer side of the eclipse-attributed penumbra region 33 in the array direction Da.

The attenuation-attributed penumbra region 46 and the eclipse-attributed penumbra region 33 each have lower X-ray intensity than the main exposed region 38, and the X-ray intensity thereof varies in the array direction Da. Therefore, the attenuation-attributed penumbra region 46 and the eclipse-attributed penumbra region 33 deteriorate the quality of the acquired image.

While FIG. 3 illustrates only the penumbra region 45 formed on the right side of the main exposed region 38 extracted from the fourth one of the apertures 9 for easy understanding, the penumbra region 45 is also formed on the left side of the main exposed region 38 and on each of two outer sides, in the array direction Da, of each of the other main exposed regions 38 extracted from the other apertures 9.

In an X-ray generating unit that includes a plurality of partitions 39 and forms an area in which main exposed regions 38 coincide with one another, it is difficult to reduce the eclipse-attributed penumbra region 33 included in the penumbra region 45.

Accordingly, the present inventors have found that the attenuation-attributed penumbra region 46 included in the penumbra region 45 is reduced by providing sloping surfaces 43 whose angles of inclination change with the positions of the partitions 39. Conditions and functional mechanisms required for reducing the attenuation-attributed penumbra region 46 by changing the angle of inclination of the sloping surfaces 43 provided to the partitions 39 will now be described.

A first condition is as follows. The forward shielding member 10 has a plurality of apertures 9 each defined by adjacent ones of the partitions 39, and a plurality of main exposed regions 38 (X-ray beams) extracted from the respective apertures 9 are oriented toward one another and made to coincide with one another with the respective center axes thereof being at different angles. Under the first condition, in the tomography in which X-ray beams are applied to the object at different angles, a wide imaging field can be defined on the examinee. In other words, for a given imaging field, the number n of targets 8 arrayed in the target array 11 can be increased while a focal spot pitch p is reduced. Thus, an effect of improving the resolution of the tomographic image in the depth direction is produced.

A second condition is as follows. The plurality of partitions 39 each have the sloping surfaces 43 extending along the plurality of main exposed regions 38 (X-ray beams). The plurality of main exposed regions 38 have respective center axes whose angles change with the positions of the respective apertures 9 provided in the forward shielding member 10. Therefore, the sloping surfaces 43 are at respective angles of inclination that change with the positions of the partitions 39 in the array direction Da. Under the second condition, regarding the X-ray beams radially emitted from the plurality of targets 8 included in the target array 11, components that are transmitted through thin corner portions of the partitions 39 are reduced, whereby the attenuation-attributed penumbra regions 46 are reduced.

Figure 4A:
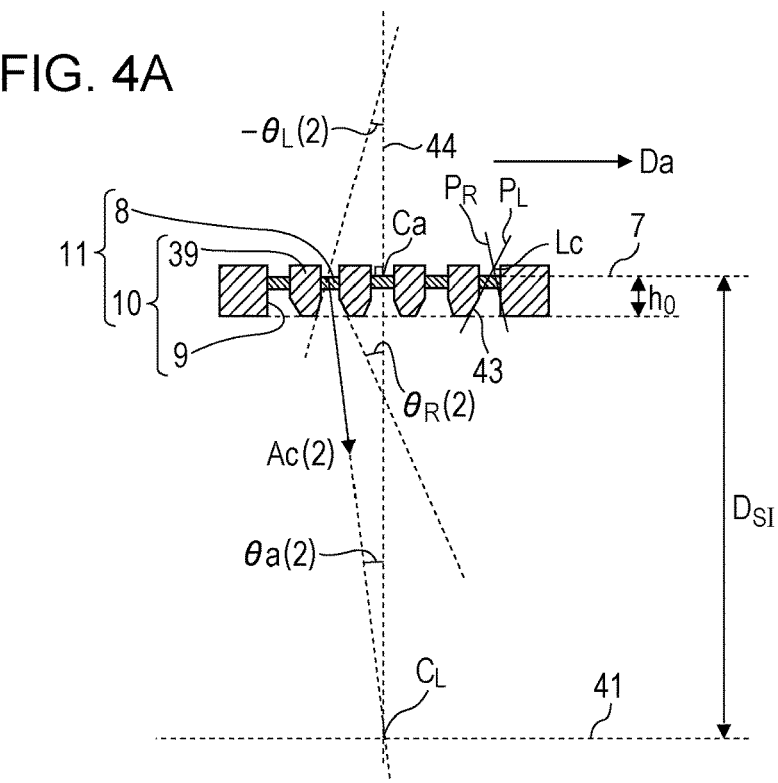
FIG. 4A is a diagram illustrating the relationship among the angles of inclination of a pair of sloping surfaces and the angle of a center axis in the X-ray generating unit according to the general embodiment of the present invention.

In the general embodiment of the present invention, as illustrated in FIG. 4A, an angle of inclination θ(i) of each of the sloping surfaces 43 can be uniquely determined by defining the angle of each sloping surface 43 with reference to the central normal line 44 in the counterclockwise direction as being positive. The central normal line 44 passes through the exposure center $C_L$ and is perpendicular to a corresponding one of the electron incident surfaces 7. Likewise, a center axis Ac(i) can also be uniquely determined by defining the angle thereof with reference to the central normal line 44 in the counterclockwise direction as being positive. Note that the suffix "i" denotes the ordinal position of each of the apertures 9 in the array direction Da.

Figure 4B:
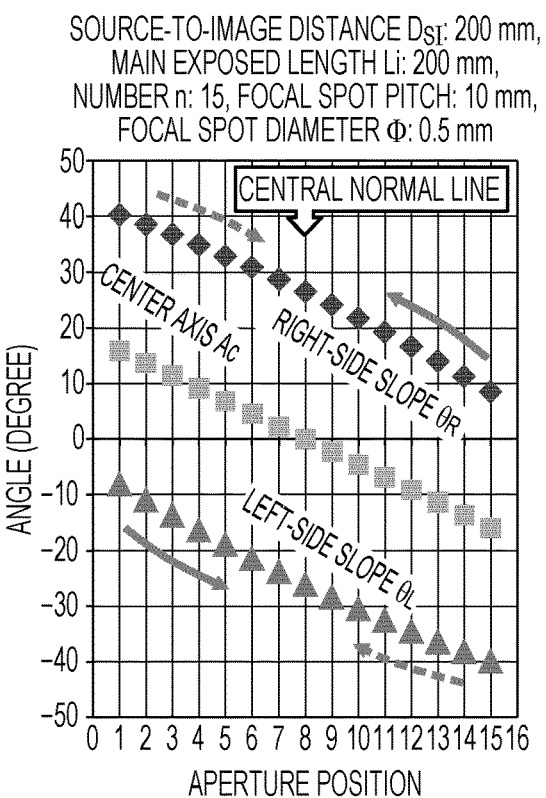
FIG. 4B is a graph illustrating the changes in the angles of inclination of the pair of sloping surfaces and in the angle of the center axis with respect to the position along an array direction according to a first exemplary embodiment of the present invention.
Figure 4C:
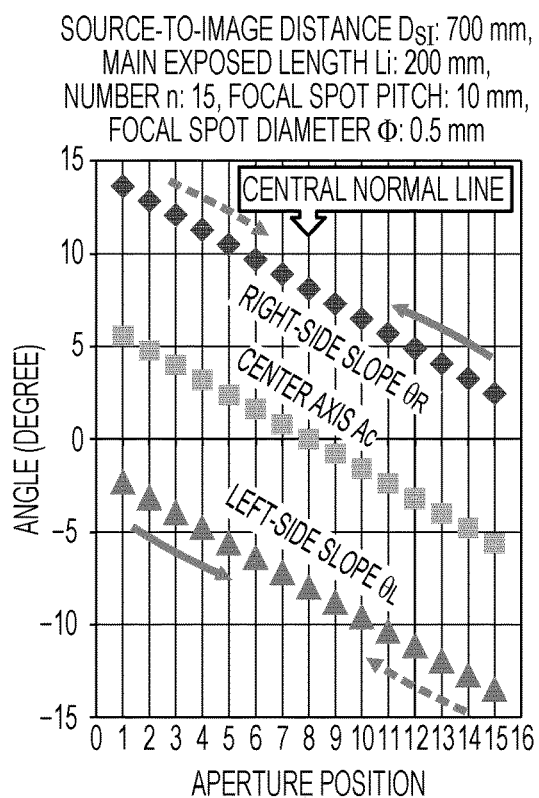
FIG. 4C is a graph illustrating the changes in the angles of inclination of the pair of sloping surfaces and in the angle of the center axis with respect to the position in the array direction according to a second exemplary embodiment of the present invention.

FIGS. 4B and 4C are graphs illustrating the changes in the angles θ(i) of the sloping surfaces 43 and in the angle of the center axis Ac(i) with respect to the position in the array direction Da according to first and second exemplary embodiments, respectively, of the present invention. Among geometrical parameters concerning the target array 11 illustrated in FIG. 4A, only a source-to-image distance $D_{SI}$ is different between that of the first exemplary embodiment and that of the second exemplary embodiment.

In the first exemplary embodiment illustrated in FIG. 4B, the source-to-image distance $D_{SI}$ is 200 mm, which is equal to the length Li by which the main exposed regions 38 coincide with one another on the detecting plane 41.

In the first exemplary embodiment, an angle of inclination $θ_R(i)$ of one of the sloping surfaces 43 that is on the right side of each aperture 9 illustrated in FIG. 4A decreases from 40.3 degrees to 8.5 degrees with the increase in the ordinal position i of the aperture 9 in the array direction Da. In the first exemplary embodiment, the forward shielding member 10 has a symmetrical shape with respect to the central normal line 44 passing through the exposure center $C_L$. Therefore, an angle of inclination $θ_L(i)$ of one of the sloping surfaces 43 that is on the left side of the aperture 9 decreases from −8.5 degrees to −40.3 degrees with the increase in the ordinal position i of the aperture 9 in the array direction Da. The angle of inclination of the center axis Ac(i) decreases substantially linearly from 15.9 degrees to −15.9 degrees with the increase in the ordinal position i of the aperture 9 in the array direction Da.

In the first exemplary embodiment in which the pitch of the plurality of focal spots 13 is constant, as the ordinal position i of the aperture 9 in the array direction Da increases, the absolute value of the rate of change in the angle of inclination $θ_R(i)$ of the sloping surface 43 on the right side gradually increases while the absolute value of the rate of change in the angle of inclination $θ_L(i)$ of the sloping surface 43 on the left side gradually decreases.

On the other hand, with the increase in the ordinal position i of the aperture 9 in the array direction Da, the rate of change in the angle of inclination of the center axis Ac(i) becomes the largest around the array center Ca. In other words, in the target array 11 according to the first exemplary embodiment, the absolute values of the angles of inclination of the center axes Ac1 to Ac5 with respect to the central normal line 44 increase with the distances from the central normal line 44 to the apertures 9.

The change in the angle of inclination of the sloping surface 43 with the position in the array direction Da is symmetrical with respect to the central normal line 44 passing through the exposure center $C_L$. Therefore, the positional relationship between the central normal line 44 and the sloping surface 43 can be interpreted as follows.

The absolute value of the angle of inclination of each of those sloping surfaces 43 of the partitions 39 that faces the central normal line 44 increases, as illustrated by the solid-line arrows in FIG. 4B, as the distance from the sloping surface 43 to the central normal line 44 is reduced. On the other hand, the absolute value of the angle of inclination of each of those sloping surfaces 43 of the partitions 39 that stands with its back to the central normal line 44 decreases, as illustrated by the broken-line arrows in FIG. 4B, as the distance from the sloping surface 43 to the central normal line 44 is reduced.

The absolute value of the rate of change, with respect to the position in the array direction Da, in the angle of inclination of each of those sloping surfaces 43 of the partitions 39 that faces the central normal line 44 decreases, as illustrated by the solid-line arrows in FIG. 4B, as the distance from the sloping surface 43 to the central normal line 44 is reduced. On the other hand, the absolute value of the rate of change, with respect to the position in the array direction Da, in the angle of inclination of each of those sloping surfaces 43 of the partitions 39 that stands with its back to the central normal line 44 increases, as illustrated by the broken-line arrows in FIG. 4B, as the distance from the sloping surface 43 to the central normal line 44 is reduced.

The second exemplary embodiment will now be described with reference to FIG. 4C illustrating the changes in the angles θ(i) of the sloping surfaces 43 and in the angle of the center axis Ac(i) with respect to the position in the array direction Da. The geometrical parameters set forth for the target array 11 according to the second exemplary embodiment are the same as those of the first exemplary embodiment, except the source-to-image distance $D_{SI}$, which is 700 mm and is larger than the length Li.

The second exemplary embodiment differs from the first exemplary embodiment in the rate of change and in the range of change in each of the above angles of inclination. Specifically, the change with respect the ordinal position i in the array direction Da is more linear and the range of change is reduced to about 0.28 times that of the first exemplary embodiment. The reduction in the range of change in the angle of inclination of the center axis Ac(i) is substantially equal to the ratio of the source-to-image distance $D_{SI}$ between the first exemplary embodiment and the second exemplary embodiment, i.e., 200:700. The tendencies of the changes in the angles of inclination $θ_R(i)$ and $θ_L(i)$ of the sloping surfaces 43 and in the angle of inclination of the center axis Ac(i) in the first and second exemplary embodiments are qualitatively the same.

Parameters that are common to the calculation models employed in the first and second exemplary embodiments are as follows: the length Li by which the main exposed regions 38 coincide with one another on the detecting plane 41 is 200 mm, the number n of targets 8 that are arrayed is 15, the focal spot pitch p is 10 mm, and the focal spot diameter $\Phi$ is 0.5 mm.

The sloping surfaces 43 may not each necessarily extend over the entirety of a corresponding one of the partitions 39 in the height direction and may each extend only in a front end portion of the partition 39 as illustrated in FIG. 4A. If the sloping surface 43 is provided in such a manner as to extend only at the front end portion of the partition 39 in the height direction, the focal spot pitch p can be reduced, whereby the resolution of the tomographic image in the depth direction is increased. The front end portion of the partition 39 in the height direction is also regarded as a portion of the partition 39 that is on a side of the aperture 9 and away from the electron incident surface 7.

As illustrated in FIG. 4A, each pair of sloping surfaces 43 that are on two sides of the center axis Ac(i) incline with respect to a line normal to a corresponding one of the electron incident surfaces 7 such that virtual planes $P_R$ and $P_L$ that are extended from the pair of sloping surfaces 43 toward a corresponding one of the targets 8 form an intersecting virtual line $L_C$ located between the electron incident surface 7 and the electron emission source 14 (not shown in FIG. 4A). Such a configuration reduces the attenuation-attributed penumbra region 46 attributed to a portion of the partition 39 at an end of the sloping surface 43 that is nearer to the target 8. In FIG. 4A, the electron emission source 14, illustrated in FIG. 1A, that faces the electron incident surfaces 7 is not illustrated.

Figure 5A:
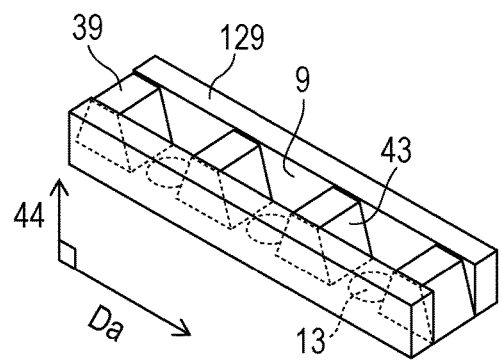
FIG. 5A is a schematic diagram of a forward shielding member included in the X-ray generating unit according to the general embodiment of the present invention.

FIG. 5A is an enlarged perspective view illustrating a part of the forward shielding member 10 included in the X-ray generating unit 2 according to the general embodiment of the present invention. As illustrated in FIG. 5A, the apertures 9 are each defined by a pair of opposite sloping surfaces 43 and side surfaces of a pair of opposite connecting portions 129. The aperture 9 according to the general embodiment has a truncated pyramid shape defined by the two sloping surfaces 43 inclining with respect to the central normal line 44, a lower plane defined by vertices V1 to V4, and an upper plane defined by vertices V5 to V8.

Figure 5B:
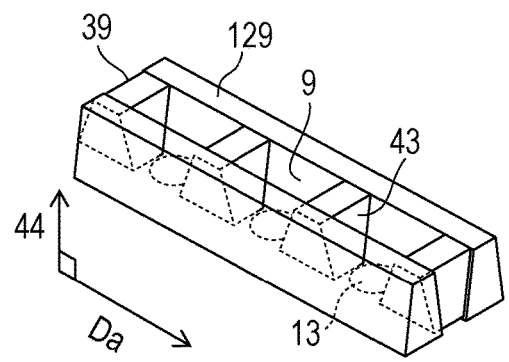
FIG. 5B is a schematic diagram of a forward shielding member included in an X-ray generating unit according to a modification of the general embodiment of the present invention.
Figure 5C:
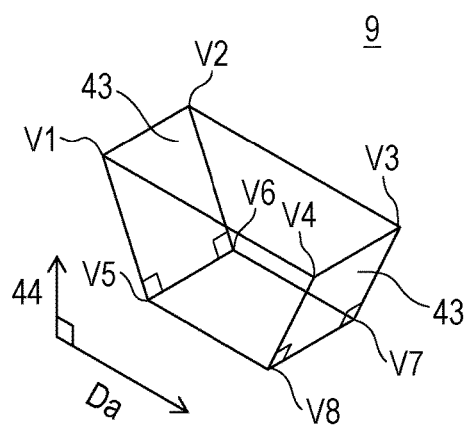
FIG. 5C is an enlarged view illustrating one of apertures of the forward shielding member according to the general embodiment of the present invention.
Figure 5D:
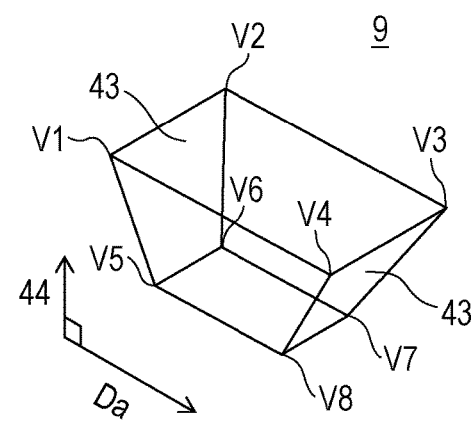
FIG. 5D is an enlarged view illustrating one of apertures of the forward shielding member according to the modification of the general embodiment of the present invention.

FIG. 5B illustrates a modification of the general embodiment illustrated in FIG. 5A. In the modification, the two planes defined by the vertices V1, V5, V8, and V4 and by the vertices V2, V6, V7, and V3 on the side surfaces of the connecting portions 129 that define the aperture 9 each incline in such a manner as to intersect the central normal line 44. The aperture 9 according to the modification has a truncated pyramid shape with four inclined planes, exclusive of the lower plane defined by the vertices V1 to V4 and the upper plane defined by the vertices V5 to V8. In the modification, the size of an area on the detecting plane 41 that is defined by the attenuation-attributed penumbra region 46 can be reduced in a direction intersecting the array direction Da. As another modification (not illustrated), the two planes defined by the vertices V1 to V4 and the vertices V5 to V8 may not necessarily be parallel to each other. That is, the aperture 9 has a pyramid shape that is defined by two or more inclined planes including at least a pair of sloping surfaces 43.

The forward shielding member 10 has at least a function of shielding the examinee or the radiologist from part of the X-rays generated by the targets 8. The forward shielding member 10 may also has a function of holding the plurality of targets 8, and a function as an electrode that defines the anode potential of the plurality of targets 8, as in the general embodiment.

The targets 8 are each a transmission-type target having the electron incident surface 7 and the emitting surface that is opposite the electron incident surface 7 and from which X-rays are emitted. As illustrated in FIGS. 1A and 1B, the transmission-type targets 8 separate incident paths along which the electron beams 12 are incident on the targets 8 from extraction paths along which the main exposed regions 38 are extracted from the targets 8. In the general embodiment, the forward shielding member 10 encloses the targets 8 and is connected to the targets 8 in such a manner as to avoid the above paths.

The target array 11 according to the general embodiment including the transmission-type targets 8 and the forward shielding member 10 is superior to a target array including reflection-type targets in terms of reducing crosstalk that may occur in the array direction Da. Such crosstalk includes at least one of backscattered electrons, backscattered X-rays, and X-rays emitted frontward.

In the case of the transmission-type targets 8, a shielding member can be positioned near the targets 8. In this respect also, the transmission-type targets 8 are superior to the reflection-type targets in terms of reducing the weight and volume of the shielding member and reducing the size of the X-ray generating unit.

While the electron source 14 according to the general embodiment is provided as a cathode array in which the plurality of electron emitting portions 32 are arrayed in correspondence with the respective targets 8, various modifications of the electron source 14 are also within the scope of the present invention. For example, the electron source 14 may include at least one electron emitting portion 32 provided with a deflection electrode. In such a modification, the electron beam 12 emitted from the single electron emitting portion 32 can be scanningly moved in the array direction Da of the target array 11. In the modification, the number of electron emitting portions 32 is made smaller than the number n of targets 8 that are arrayed. Therefore, the misalignment between the electron emitting portions 32 and the targets 8 or the variation in the current-voltage (IV) characteristics of the electron emitting portions 32 are suppressed.

In the general embodiment, the target array 11 is connected to an envelope 37 at an opening of the envelope 37 such that the electron incident surfaces 7 face toward an internal space 40. In the general embodiment, the target array 11 also serves as one of structural members constituting the envelope 37, and the targets 8 are also regarded as windows from which the X-rays are emitted.

The electron emitting portions 32 and the electron incident surfaces 7 are in contact with the internal space 40 of the envelope 37, which is vacuumed. In such a configuration, scattering of the electron beams 12 from the electron emitting portions 32 that is caused by gas molecules is suppressed, and the electron beams 12 are assuredly allowed to be incident on the electron incident surfaces 7. Hence, the entirety of the electron emission source 14 or the entirety of the target array 11 may not necessarily be housed in the envelope 37. That is, part of the electron emission source 14 or part of the target array 11 exclusive of the electron emitting portions 32 or the electron incident surfaces 7 may be exposed to the outside of the envelope 37. The degree of vacuum of the internal space 40 can be set within $10^{-8}$ Pa or higher and $10^{-4}$ Pa or lower for stable emission of electrons.

The envelope 37 can be made of a material having fastness so as to be resistant to atmospheric pressure and also having air-tightness so as to maintain the vacuum. Specifically, the envelope 37 can be made of brass, stainless steel, aluminum, copper, or the like. As illustrated in FIG. 1A, the envelope 37 according to the general embodiment is provided with a current introducing terminal 30 that electrically connects the electron source 14 and a driving circuit 22 to each other. The current introducing terminal 30 may electrically connect the target array 11 and the driving circuit 22 to each other as illustrated in FIG. 1A, or may electrically connect the target array 11 and a ground terminal (not illustrated) to each other.

A radiographic apparatus 1 according to a third exemplary embodiment of the present invention to which the X-ray generating unit 2 according to the general embodiment is applied will now be described with reference to FIG. 6. In the third exemplary embodiment, the radiographic apparatus 1 includes at least the X-ray generating unit 2, an X-ray detecting unit 3, and an object positioning portion 4. The X-ray detecting unit 3 faces toward the target array 11. The object positioning portion 4 is provided between the X-ray generating unit 2 and the X-ray detecting unit 3 and on the X-ray detecting unit 3.

The object positioning portion 4 is a space in which an object 25 can be positioned. The object 25 may be a part of a human body such as a breast, a limb, or the head of the examinee; a living thing; an organism for biopsy; and so forth. If the object 25 is a breast, the object positioning portion 4 and the radiographic apparatus 1 function as a breast inserting portion 5 and a mammotomographic apparatus, respectively.

The X-ray detecting unit 3 includes at least a detecting portion 15 and shielding portions 16. A plurality of detecting devices (not illustrated) are provided in the detecting portion 15. The plurality of detecting devices are arrayed two-dimensionally in the detecting portion 15, whereby a two-dimensional image is acquired.

The shielding portions 16 are provided on the respective outer sides of the detecting portion 15 in the array direction Da and each include at least a member that shields the examinee or the radiologist from X-rays.

The technical significance of the shielding portions 16 will now be described.

The X-ray generating unit 2 including the forward shielding member 10 generates, on a side thereof on which the X-ray detecting unit 3 and the forward shielding member 10 face each other, main exposed regions 38 each having a focal spot that is not eclipsed and eclipse-attributed penumbra regions 33 each having a focal spot that is partially eclipsed. The eclipse-attributed penumbra regions 33 are not reduced by the forward shielding member 10 having the sloping surfaces 43 whose angles of inclination change. Therefore, the main exposed regions 38 are each accompanied by two eclipse-attributed penumbra regions 33 produced on two respective outer sides thereof in the array direction Da. That is, as illustrated in FIG. 6, the radiographic apparatus 1 according to the third exemplary embodiment applies main X-ray beams and eclipse-attributed penumbra beams to the X-ray detecting unit 3 and thus forms a main exposed area having a length Li and eclipsed-attributed penumbra areas on the X-ray detecting unit 3, the eclipse-attributed penumbra areas being formed on the two respective outer sides of the main exposed area.

As described above, the eclipse-attributed penumbra regions 33 are unnecessary components of X-rays and each spread toward the outer side of the main exposed area, which is necessary for acquiring a radiographic image. Therefore, the eclipse-attributed penumbra regions 33 tend to leak to the outside of the radiographic apparatus.

To suppress the leakage of the eclipse-attributed penumbra regions 33 to the outside of the radiographic apparatus, the entirety of the radiographic apparatus may be covered with a shielding member. In such a configuration, however, the weight of the radiographic apparatus may increase and the center of gravity of the radiographic apparatus may be raised. Consequently, in the case where the entirety of the radiographic apparatus is covered with a shielding member, the radiographic apparatus becomes unstable with unbalanced weight distribution, increasing the probability of image blurring during imaging.

Alternatively, the shielding member may be extended beyond the outer periphery of the X-ray generating unit toward the outer periphery of the X-ray detecting unit. In such a configuration also, image blurring during imaging tends to occur because of the reduced stability with unbalanced weight distribution of the radiographic apparatus that is attributed to the increase in weight and the raising of the center of gravity.

The above two alternative configurations each have a problem in that the shielding member becomes tall and gives the examinee a sense of oppression near his/her upper body, and reduces the ease of operation to be performed by the radiologist.

The present inventors have quantified the range of each eclipse-attributed penumbra region 33 on the basis of the geometric dimensions of the forward shielding member 10 included in the X-ray generating unit 2 and the distance between the forward shielding member 10 and the detecting portion 15 included in the X-ray detecting unit 3. Furthermore, on the basis of the quantified range of the eclipse-attributed penumbra region 33, the present inventors have found a specific configuration in which the occurrence of any eclipse-attributed penumbra regions 33 that may go past the X-ray detecting unit 3 is effectively reduced with a reduced proportion of the shielding members.

In the specific configuration according to the present invention, the eclipse-attributed penumbra regions 33 can be reduced without reducing the stability in terms of weight distribution of the radiographic apparatus 1, whereby the radiographic apparatus 1 can provide superior imaging performance and usability.

The eclipse-attributed penumbra regions 33 each have a specific spatial size in the array direction Da that depends on a focal spot diameter $\Phi$ as the size of each focal spot 13 in the array direction Da, the height $h_0$ of the partitions 39, and a source-to-image distance $D_{SI}$ as the distance from the targets 8 to the detecting portion 15. If the height $h_0$ of the partitions 39 is set to the same value as the source-to-image distance $D_{SI}$, the eclipse-attributed penumbra regions 33 can be eliminated theoretically. In such a case, however, the plurality of main exposed regions 38 do not coincide with one another on a detecting plane 41. To allow the plurality of main exposed regions 38 to coincide with one another on the detecting plane 41, the height $h_0$ of the partitions 39 is limited to a predetermined maximum height $h_{max}$ or smaller.

As illustrated in FIG. 4A, the height $h_0$ is defined as the length of the partitions 39 from the electron incident surfaces 7 in the direction of the central normal line 44 with respect to the electron incident surfaces 7. The detecting plane 41 contains the detecting portion 15 and is defined as a virtual plane spreading around the detecting portion 15.

Figure 6:
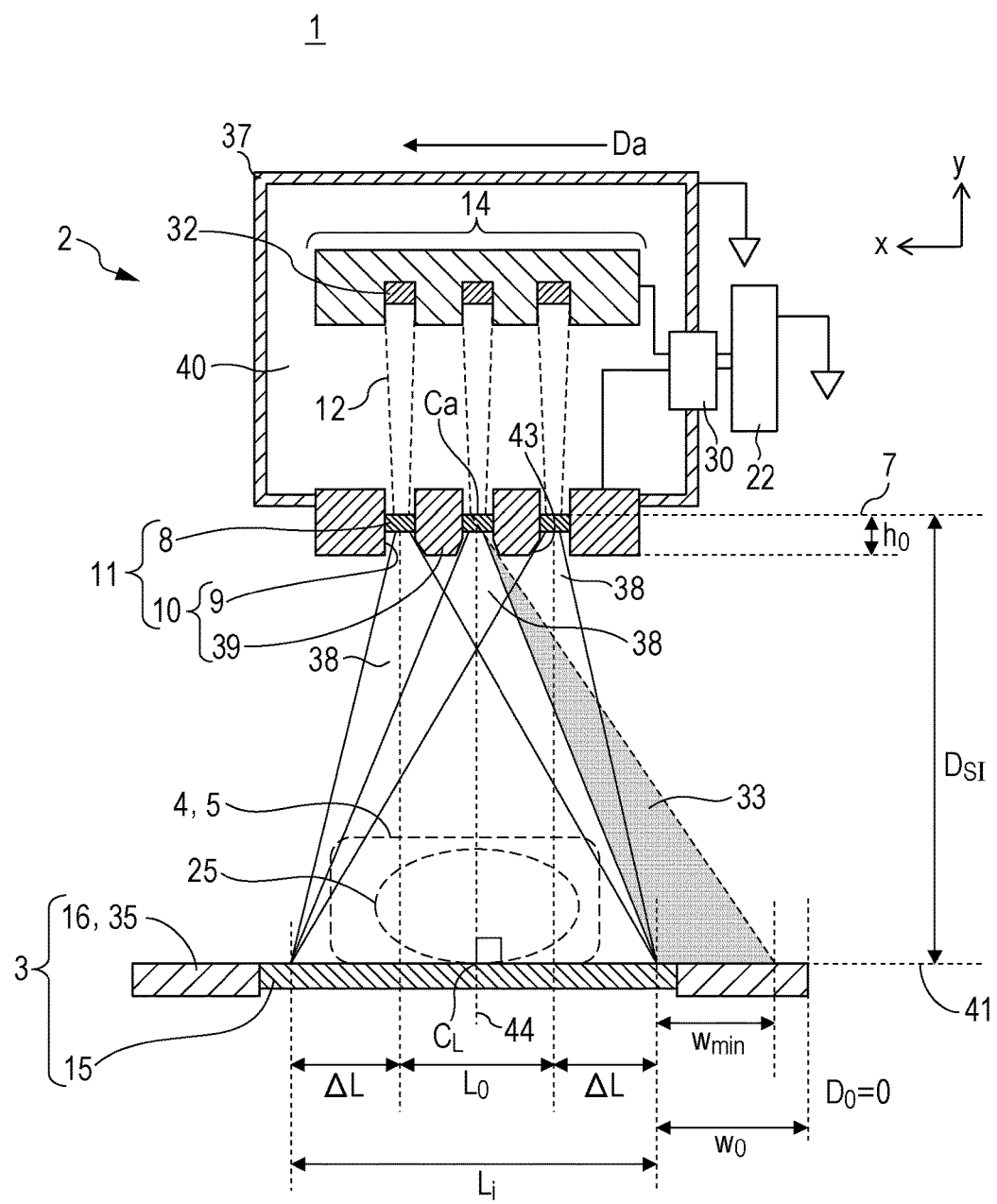
FIG. 6 is a schematic diagram of a radiographic apparatus according to a third exemplary embodiment of the present invention.

If the detecting portion 15 is a flat plane as illustrated in FIG. 6, the detecting plane 41 is defined as a virtual flat plane containing the detecting portion 15. If the detecting portion 15 is parallel to the electron incident surfaces 7 as illustrated in FIG. 6, the detecting plane 41 is uniquely determined as a virtual plane whose normal line corresponds to a perpendicular line 19 extending perpendicularly from the array center Ca, in the array direction Da, of the target array 11 toward the detecting portion 15.

As illustrated in FIG. 6, the shielding portions 16 are provided on the respective outer sides of the detecting portion 15 in the array direction Da and on the respective outer sides of an area in which the main exposed regions 38 coincide with one another by a length Li on the X-ray detecting unit 3. The shielding portions 16 can be made of a material having high X-ray absorptance. The shielding portions 16 may alternatively be made of metal such as stainless steel or aluminum, as long as the shielding portions 16 each have a thickness that can attenuate the X-rays by a required amount. The shielding portions 16 can each be provided as a member containing at least any one of the following metallic elements: lead, gold, platinum, silver, tungsten, molybdenum, tantalum, copper, nickel, iron, titanium, silicon carbide, and aluminum.

In the third exemplary embodiment illustrated in FIG. 6, the shielding portions 16 each include an outer shielding portion 35 that extends on the outer side of the detecting portion 15 in the array direction Da. The shielding portions 16 according to the third exemplary embodiment each have a predetermined width $w_0$. A height $D_0$ of each of the shielding portions 16 with respect to the detecting plane 41 is zero.

In the third exemplary embodiment, the outer shielding portion 35 is provided in an area having the width $w_0$, the area extending toward the outer side in the array direction Da by a length larger than a length $w_{min}$ of the eclipse-attributed penumbra region 33 on the detecting plane 41. The length $w_{min}$ is the length of the eclipse-attributed penumbra region 33 in a case where the shielding portions 16 are not provided. Therefore, in the third exemplary embodiment, at least the eclipse-attributed penumbra regions 33 are produced within an area over which the X-ray detecting unit 3 extends. Hence, the leakage of the eclipse-attributed penumbra regions 33 to the outside of the radiographic apparatus 1 is reduced.

As described above, in the radiographic apparatus 1 including the plurality of targets 8 and the partitions 39 that separate the targets 8 from one another, the shielding portions 16 are technically significant in effectively reducing the leakage of at least the eclipse-attributed penumbra regions 33 to the outside with a reduced proportion of the shielding members.

Now, conditions for the height $D_0$ and the width $w_0$ of the shielding portions 16 that are required for producing the effect of reducing the leakage of at least the eclipse-attributed penumbra regions 33 to the outside will be described. The height $D_0$ and the width $w_0$ of the shielding portions 16 and the height $h_3$ of the partitions 39 are defined complementarily to one another as described below.

The third exemplary embodiment indicates that the present invention includes not only a case where the height $D_0$ is 0 but also a case where the height D is larger than 0. The shielding portions 16 each have a predetermined height $D_0$ that is larger than zero, the height $D_0$ and the width $w_0$ of the shielding portions 16 and the height $h_0$ of the partitions 39 complementarily satisfy Expressions (1) to (3) given below. Details will now be described.

In the third exemplary embodiment, the height $h_0$ of the partitions 39 satisfies Expression (1):

[Math. 1]

$$h_0 \le h_{max} = \frac{p}{p+Li} D_{SI} \qquad (1)$$

where p denotes the focal spot pitch, and Li denotes the length by which the main exposed regions 38 coincide with one another on the detecting plane 41. By making the focal spot pitch p sufficiently large relative to the length Li, the main exposed regions 38 can be made to coincide with one another on the detecting plane 41 even if the height $h_0$ of the partitions 39 is as large as the source-to-image distance $D_{SI}$. However, increasing the focal spot pitch p means limiting the resolution in the depth direction in the tomography. Therefore, the focal spot pitch p is preferably a small value relative to the length Li, more preferably, smaller than 1/10 of the length Li. Hence, the height $h_0$ is limited to a value that is sufficiently smaller than the source-to-image distance $D_{SI}$.

Letting the main exposed length, which is the length of the main exposed area defined by a single main exposed region 38, be Lm, the length Li by which main exposed areas defined by the plurality of main exposed regions 38 coincide with one another satisfies a relationship of Li≤Lm. In this specification, the length by which the main exposed areas defined by the respective main exposed regions 38 coincide with one another and the length by which the main exposed regions 38 coincide with one another on the detecting plane 41 are the same.

Letting the length of the array of the targets 8 be $L_0$ and the length of each of portions of the main exposed area that spread toward the respective outer sides beyond the area defined by the length $L_0$ be ΔL, the main exposed length Lm is expressed as Lm=$L_0$+2×ΔL. Note that the array length $L_0$ is uniquely defined as the distance between the centers of two focal spots 13 formed by two targets 8 that are at the extreme ends, respectively, of the target array 11.

Letting the diameter of the focal spots 13, the number of targets 8 included in the target array 11, and the diameter of the apertures 9 provided in the forward shielding member 10 be Φ, n, and Ψ, respectively, $L_0$=(n−1)×p and ΔL=½×{Φ+($D_{SI}/h_0$)×(Ψ−Φ)} hold. Hence, the main exposed length Lm in the array direction Da is expressed by (n−1)×p+{Φ+($D_{SI}/h_0$)×(Ψ−Φ)}.

Here, the focal spot diameter Φ is a diameter of each of the focal spots 13 in the array direction Da, the number n is the number of targets 8 included in the target array 11, and the aperture diameter Ψ is the length, in the array direction Da, of each of the apertures 9 provided in the forward shielding member 10.

Expression (1) means that the height $h_0$ of the partitions 39 included in the forward shielding member 10 is smaller than or equal to the maximum height $h_{max}$ given on the right side of the sign of inequality in Expression (1). If the height $h_0$ of the partitions 39 included in the forward shielding member 10 satisfies Expression (1), the X-ray generating unit 2 can make the main exposed areas coincide with one another by the length Li on the detecting plane 41 of the X-ray detecting unit 3.

To allow the X-ray beams corresponding to the main exposed regions 38 to be applied to the object 25 from different angles, the partitions 39 each include at least a member that shields the examinee or the radiologist from X-rays. Specifically, the partitions 39 each contain at least any one of the following metallic elements: lead, gold, platinum, silver, tungsten, molybdenum, tantalum, copper, nickel, and iron.

Now, conditions for the width $w_0$ and the height Dc of the shielding portions 16 will be described specifically. The width $w_0$ and the height $D_0$ of the shielding portions 16 satisfy Expressions (2) and (3), respectively:

[Math. 2]

$$w_0 \geq w_{min} = \frac{D_{SI} - h_0}{h_0} \Phi \quad (2)$$

[Math. 3]

$$D_0 < 2\Phi \cdot D_{SI} \cdot \left(\frac{D_{SI} - h_0}{2D_{SI}\Phi + h_0(\Psi - \Phi)}\right) \cdot \left(1 - \frac{w_0}{\Phi} \times \frac{h_0}{D_{SI} - h_0}\right) \quad (3)$$

Expression (3) represents a condition that the effect of reducing the leakage of eclipse-attributed penumbra regions 33 cannot be produced only by defining the height $D_0$ of the shielding portions 16. Under the condition represented by Expression (3), if the width $w_0$ is larger than or equal to the minimum width (the length of the eclipse-attributed penumbra region 33) $w_{min}$ given on the right side of the sign of inequality in Expression (2), the leakage of the eclipse-attributed penumbra regions 33 can be reduced by the shielding portions 16 that include the respective outer shielding portions 35 as illustrated in FIG. 6.

The length $w_{min}$ of the eclipse-attributed penumbra region 33 is the length of an area to which the penumbra regions 33 are applied to the detecting plane 41 in the case where the height $D_0$ of the shielding portions 16 is zero. The length $w_{min}$ of the eclipse-attributed penumbra region 33 corresponds to the length of an area that extends toward the outer side in the array direction Da by a length expressed as $\{(D_{SI}-h_0)/h_0\}\times p$ from the edge of the main exposed area.

A radiographic apparatus 1 according to a fourth exemplary embodiment of the present invention will now be described with reference to FIG. 7, focusing on a relationship to be satisfied among the height $h_0$ of the partitions 39 and the width $w_0$ and the height $D_0$ of the shielding portions 16. The fourth exemplary embodiment differs from the third exemplary embodiment in that the shielding portions 16 includes the outer shielding portions 35 and upright shielding portions 36. The outer shielding portions 35 extend on the outer sides, respectively, of the detecting portion 15 in the array direction Da. The upright shielding portions 36 extend from the detecting plane 41 toward the target array 11. In the fourth exemplary embodiment, the shielding portions 16 have a predetermined height $D_0$ and a predetermined width $w_0$.

In the fourth exemplary embodiment also, the height $h_0$ of the partitions 39 needs to satisfy the condition that the main exposed regions 38 coincide with one another on the detecting plane 41 while forming a main exposed area having the length Lm containing the predetermined length Li. Hence, the height $h_0$ of the partitions 39 needs to satisfy Expression (1) given in the third exemplary embodiment.

Figure 7:
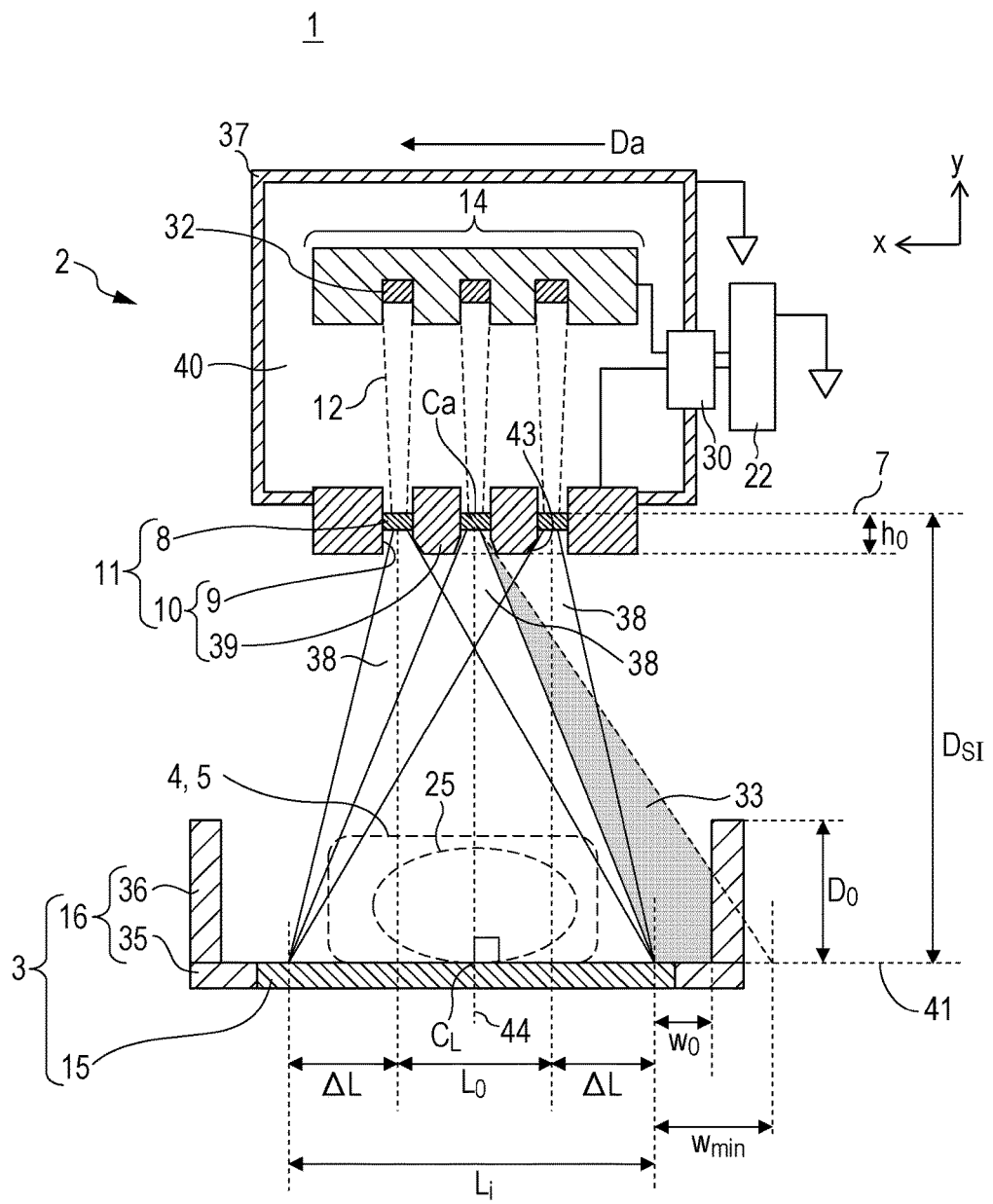
FIG. 7 is a schematic diagram of a radiographic apparatus according to a fourth exemplary embodiment of the present invention.

In the fourth exemplary embodiment illustrated in FIG. 7, the shielding portions 16 have a width that is smaller than the minimum width $w_{min}$ defined by the right side of Expression (2). The width $w_0$ and the height $D_0$ of the shielding portions 16 included in the X-ray detecting unit 3 according to the fourth exemplary embodiment satisfy Expressions (4) and (5), respectively:

[Math. 4]

$$w_0 < w_{min} = \frac{D_{SI} - h_0}{h_0} \Phi \quad (4)$$

[Math. 5]

$$D_0 \geq 2\Phi \cdot D_{SI} \cdot \left(\frac{D_{SI} - h_0}{2D_{SI}\Phi + h_0(\Psi - \Phi)}\right) \cdot \left(1 - \frac{w_0}{\Phi} \times \frac{h_0}{D_{SI} - h_0}\right) \quad (5)$$

Expression (4) represents a condition that the effect of reducing the leakage of the eclipse-attributed penumbra regions 33 cannot be produced only by defining the width $w_0$ of the shielding portions 16. Under the condition represented by Expression (4), if the height $D_0$ of the shielding portions 16 is larger than or equal to the minimum value given on the right side of Expression (5), the leakage of the eclipse-attributed penumbra regions 33 can be reduced by the shielding portions 16 that include the outer shielding portions 35 and the upright shielding portions 36 as illustrated in FIG. 7. Hence, in the fourth exemplary embodiment also, the width $w_0$ and the height $D_0$ of the shielding portions 16 and the height $h_0$ of the partitions 39 are defined complementarily to one another, as in the third exemplary embodiment.

As described above, in the third or fourth exemplary embodiment, the shielding portions 16 each include at least a part extending in the eclipse-attributed penumbra region 33 and a part overlapping the eclipse-attributed penumbra area on the detecting plane 41; or the shielding portions 16 each include a part extending on the outer side of the eclipse-attributed penumbra region 33 in the array direction Da and a part extending along the detecting plane 41 and on the outer side of the eclipse-attributed penumbra area. Extending on the outer side in the array direction Da means extending over an area that is farther than the eclipse-attributed penumbra area from the perpendicular line 19 extending from the array center Ca of the target array 11 toward the detecting portion 15.

The present invention also encompasses an embodiment in which the X-ray detecting unit 3 includes the shielding portion 16 according to the third exemplary embodiment on one of the two outer sides in the array direction Da and the shielding portion 16 according to the fourth exemplary embodiment on the other outer side in the array direction Da.

The length Li by which the plurality of main exposed regions 38 coincide with one another on the detecting plane 41 can be identified by sequentially applying the electron beams 12 to the respective targets 8 and measuring the main exposed length Lm in the array direction Da for each of the electron beams 12. The main exposed area and the eclipse-attributed penumbra area can be identified by providing a pinhole mask between the targets 8 and the X-ray detecting unit 3 and measuring the focal images.

As described in each of the third and fourth exemplary embodiments concerning the radiographic apparatus 1, the shielding portions 16 can be provided in various other ways, as long as the shielding portions 16 are provided in areas where the leakage of at least the eclipse-attributed penumbra regions 33 included in the penumbra regions 45 is reduced.

The present invention encompasses an embodiment in which a pair of shielding portions 16 are provided on two respective outer sides of the detecting portion 15 in the array direction Da, as illustrated in FIG. 6 or 7.

The height $h_0$ of the partitions 39 satisfies Expression (6) given below. Thus, the width of each penumbra region 33 along the array direction Da is reduced, leading to a size reduction of the radiographic apparatus 1.

[Math. 6]

$$h_0 \geq \frac{1}{10} \frac{p}{p+Li} D_{SI} \qquad (6)$$

From the viewpoint of the size reduction of the radiographic apparatus 1, the height $h_0$ of the partitions 39 is more preferably within a range from 2 mm or larger to 20 mm or smaller.

The shielding portions 16 only need to be included in the X-ray detecting unit 3 in such a manner as to be positioned in the respective eclipse-attributed penumbra regions 33. As illustrated in FIG. 6 or 7, the outer end of each of the shielding portions 16 in the array direction Da may extend by the width $w_0$, i.e., up to a position on the outer side of a corresponding one of the eclipse-attributed penumbra regions 33. In the third or fourth embodiment illustrated in FIG. 6 or 7, the inner end of each of the shielding portions 16 in the array direction Da is positioned on the outer side of an area defined by the length Li corresponding to the main exposed length Lm. Alternatively, the inner end of the shielding portion 16 in the array direction Da may overlap an end portion of the area defined by the length Li, or may be positioned on the inner side of the area defined by the length Li.

If the inner end of the shielding portion 16 is positioned on the inner side of the area defined by the length Li, the inner end of the shielding portion 16 is desirably positioned in an area that does not overlap a site of interest of the object 25. Compared with a configuration (not illustrated) in which the examinee or the radiologist is shielded from eclipse-attributed penumbra regions 33 by the detecting portion 15 and the shielding portions 16, the configuration according to any of the above exemplary embodiments in which the examinee or the radiologist is shielded from the eclipse-attributed penumbra regions 33 only by the shielding portion 16 allows high-cost X-ray detecting devices to be provided at a higher density in the area defined by the length Li by which the main exposed regions 38 coincide with one another. Consequently, according to any of the above exemplary embodiments, the radiographic apparatus 1 can be provided with a higher imaging resolution and at a lower cost.

Figure 8:
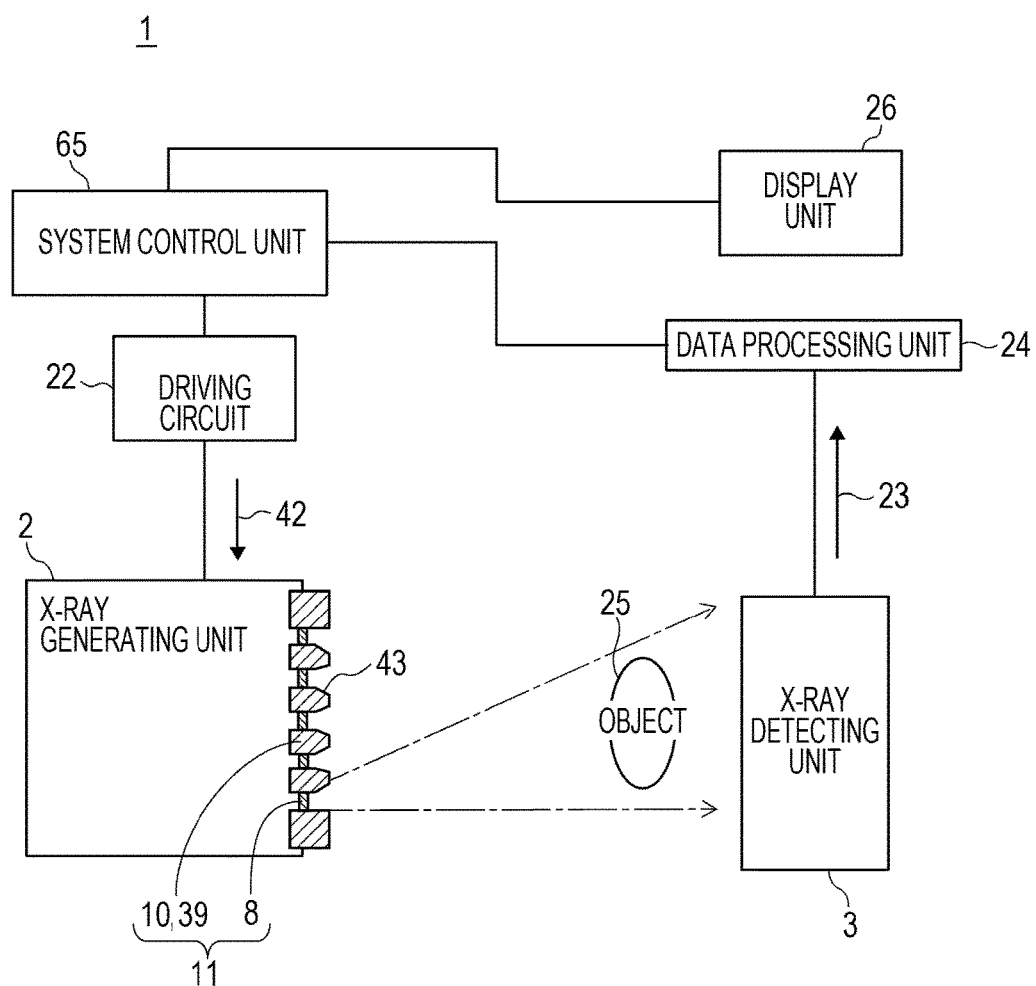
FIG. 8 is a system diagram of the radiographic apparatus according to the general embodiment of the present invention.

An exemplary system configuration of the radiographic apparatus 1 according to the general embodiment of the present invention will now be described with reference to FIG. 8.

The X-ray generating unit 2 and the X-ray detecting unit 3 are controlled in conjunction with each other by a system control unit 65. The driving circuit 22, which is controlled by the system control unit 65, outputs a control signal 42 to the X-ray generating unit 2. In accordance with the control signal 42, the state of emission of the X-ray beams emitted from the X-ray generating unit 2 is controlled. The X-ray beams emitted from the X-ray generating unit 2 are transmitted through the object 25 and are detected by the X-ray detecting unit 3. The X-ray detecting unit 3 converts the detected X-ray beams into a radiographic image 23 and outputs the radiographic image 23 to a data processing unit 24. The data processing unit 24, which is controlled by the system control unit 65, performs a predetermined signal processing operation on the radiographic image 23 and outputs the radiographic image 23 thus processed to the system control unit 65. In receipt of the radiographic image 23 that has been subjected to signal processing, the system control unit 65 outputs to the display unit 26 a display signal for displaying an image on a display unit 26. The display unit 26 displays an image that is based on the display signal on a screen as an image of the object 25.

Now, tomosynthesis imaging performed by using the radiographic apparatus 1 according to the general embodiment will now be described with reference to FIG. 8. In tomosynthesis imaging, X-ray beams are sequentially applied to the object 25 from the plurality of targets 8. The X-ray beams that have been transmitted through the object 25 are detected by the X-ray detecting unit 3, whereby a plurality of images are taken. The plurality of images thus taken are reconstructed by the data processing unit 24, whereby a tomographic image is formed.

In the third or fourth exemplary embodiment illustrated in FIG. 6 or 7, the object positioning portion 4 can function as a breast inserting portion 5 into which a breast of the examinee is to be inserted in a direction intersecting both the array direction Da and the perpendicular line 19. In such a configuration, the radiographic apparatus 1 according to the general embodiment of the present invention is used for mammotomography in which a plurality of images are acquired at different angles about the direction in which the mammary glands extend.

In the case where the radiographic apparatus 1 according to the general embodiment of the present invention is applied to mammotomography, the general embodiment encompasses a modification in which a pressing plate (not illustrated) is provided between the object positioning portion 4 and the forward shielding member 10. The pressing plate presses the breast by reducing the distance to the detecting portion 15, whereby the detection of any abnormal portions such as calcified portions that tend to overlap mammary glands in the thickness direction of the breast is facilitated.

Hence, according to the general embodiment of the present invention, there is provided a radiographic apparatus that has a satisfactory main exposed length Li, a satisfactory resolution in the depth direction, and reduces the leakage of the eclipse-attributed penumbra regions 33 toward the outer side in the array direction Da. With such a radiographic apparatus according to the general embodiment of the present invention, the amount of unnecessary exposure of the radiologist and the examinee to leaked X-rays is reduced, and tomography with a high resolution in the depth direction can be implemented.

Now, a radiographic apparatus according to a fifth exemplary embodiment of the present invention will be described with reference to FIGS. 9 and 10.

The fifth exemplary embodiment concerns a case where the radiographic apparatus 1 according to the general embodiment of the present invention is applied to mammotomography, and is intended to reduce unnecessary X-ray exposure of the body of the examinee. The fifth exemplary embodiment is characterized in the shape of the forward shielding member 10 included in the X-ray generating unit 2.

Figure 9:
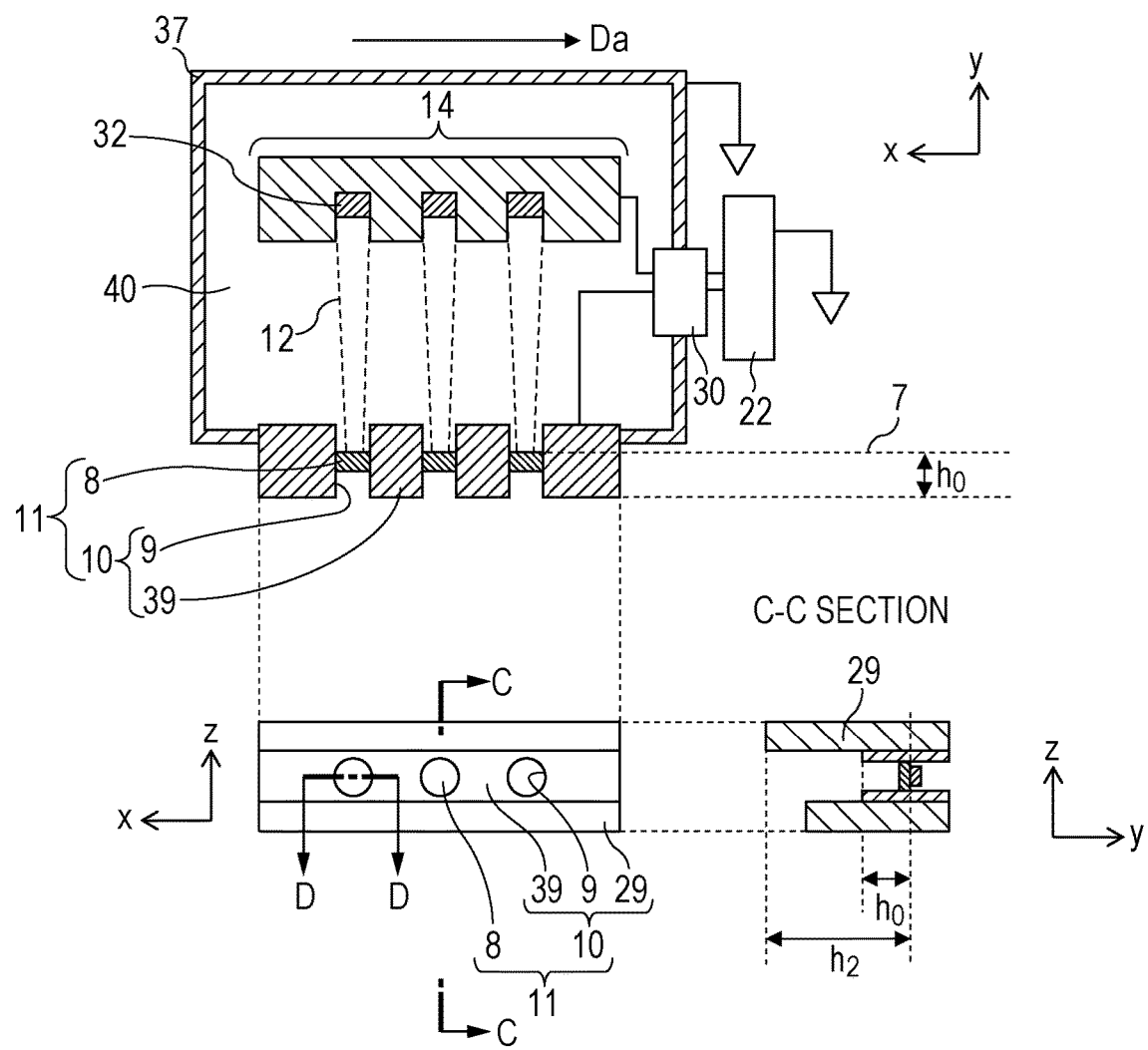
FIG. 9 is a three-way view of an X-ray generating unit included in a radiographic apparatus according to a fifth exemplary embodiment of the present invention.

FIG. 9 is a three-way view of an X-ray generating unit 2 according to the fifth exemplary embodiment. In the fifth exemplary embodiment, the forward shielding member 10 extends in the array direction Da and includes a pair of shielding walls 29 that hold the partitions 39 therebetween. At least one of the shielding walls 29 has a height $h_2$ that is larger than the height $h_0$ of the partitions 39 ($h_2 > h_0$). The height $h_2$ is defined as the length from the electron incident surfaces 7 of the targets 8 in the direction of the line normal to the electron incident surfaces 7 toward the X-ray detecting unit 3, as with the height $h_0$. The shielding walls 29 correspond to a modification of the connection portion 129 which has a property of attenuating X-rays.

Figure 10:
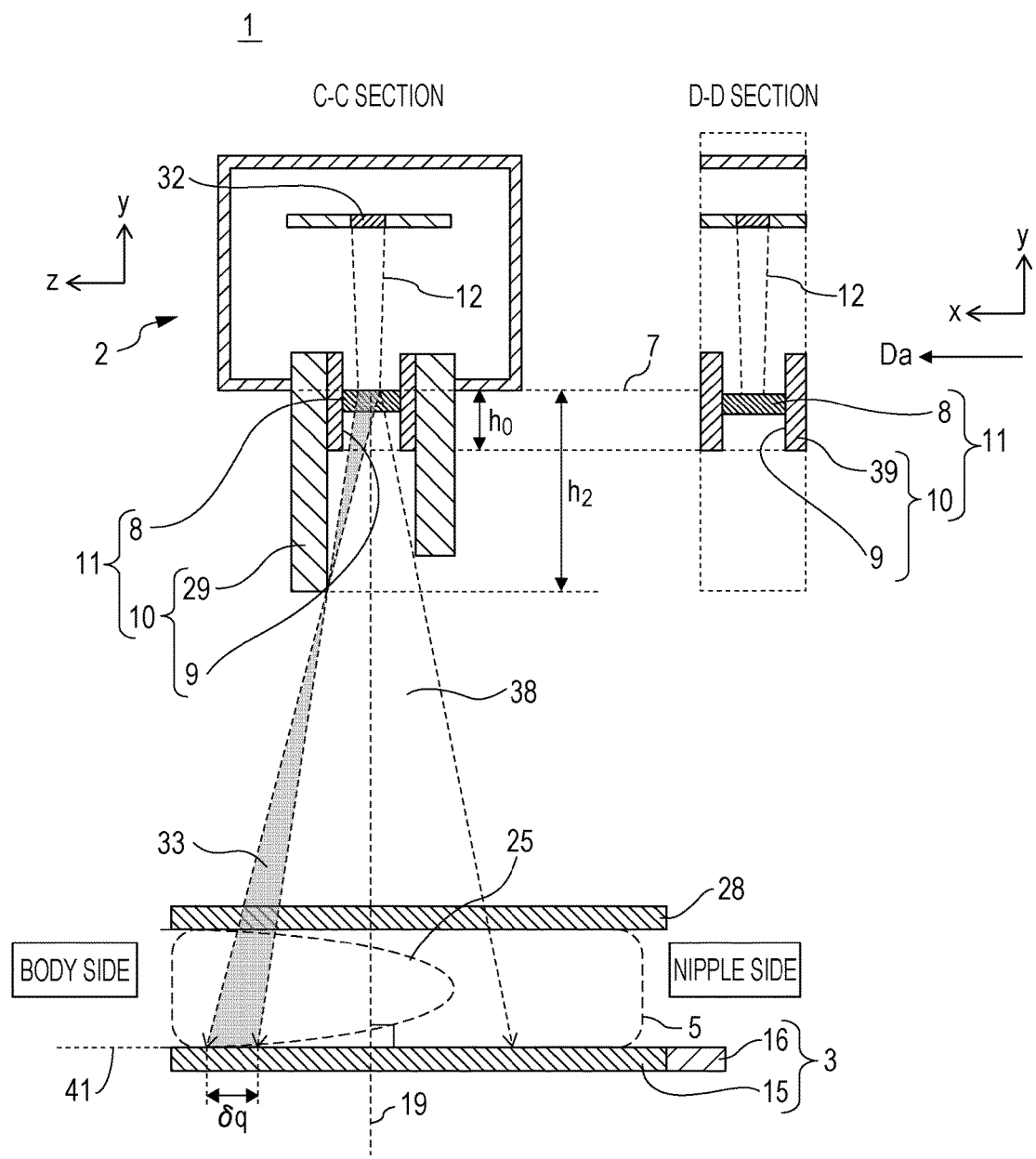
FIG. 10 is a schematic diagram of the radiographic apparatus according to the fifth exemplary embodiment of the present invention.

As illustrated in FIG. 10, in the radiographic apparatus 1 according to the fifth exemplary embodiment, one of the shielding walls 29 that has the height $h_2$ is provided on a side nearer to the body of the examinee than the apertures 9 in a direction intersecting the array direction Da. In the configuration according to the fifth exemplary embodiment, unnecessary X-ray exposure of the body of the examinee is reduced. Unnecessary X-rays include the eclipse-attributed penumbra regions 33 that are attributed to the size of the focal spots, the height of the forward shielding member 10, and the source-to-image distance. In the fifth exemplary embodiment, the eclipse-attributed penumbra regions 33 to be considered as the problem occur on the respective outer sides in the direction intersecting the array direction Da. In particular, a component that leaks toward the body of the examinee is the problem.

Letting the length of each eclipse-attributed penumbra region 33 on the detecting plane 41 in a direction perpendicular to the array direction Da be δq, if the height hz satisfies Expression (7) below, the leakage of the eclipse-attributed penumbra region 33 occurring on the outer side in the direction intersecting the array direction Da is effectively reduced.

[Math. 7]

$$h_2 \geq \frac{D_{SI} \cdot \Phi}{\delta q + \Phi} \qquad (7)$$

While FIG. 10 illustrates a case where a pair of shielding walls 29 are provided, the present invention also encompasses an embodiment in which only one of the shielding walls 29 that has the height $h_2$ ($> h_0$) is provided. In such an embodiment, the shielding wall 29 is provided on the side nearer to the body of the examinee than the apertures 9.

With the radiographic apparatus 1 according to the fifth exemplary embodiment, mammotomography is implemented with smaller eclipse-attributed penumbra regions 33 leaking toward the outer sides in the array direction Da and with a smaller eclipse-attributed penumbra region 33 leaking in the direction intersecting the array direction Da and toward the body of the examiner.

The fifth exemplary embodiment employs a pressing plate 28 provided between the breast inserting portion 5 and the forward shielding member 10. In the radiographic apparatus 1 according to the fifth exemplary embodiment, the breast is pressed by bringing the pressing plate 28 close to the detecting portion 15. Such a configuration improves the performance in detecting any abnormal portions such as calcified portions that tend to be overlooked when overlapping normal portions such as mammary glands in the direction of the perpendicular line 19.

According to any of the above embodiments of the present invention, attenuation-attributed penumbra regions attributed to the shape of the forward shielding member can be reduced. Thus, radiography that is superior in imaging performance and usability can be implemented.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-247132, filed Nov. 29, 2013, which is hereby incorporated by reference herein in its entirety.

The invention claimed is:

1. An X-ray generating unit comprising:
   a plurality of targets that are arrayed in a line;
   a forward shielding member including a plurality of partitions that each separate adjacent ones of the targets; and
   an electron source that emits electron beams to electron incident surfaces of the plurality of targets, respectively,
   wherein each partition has sloping surfaces including a first sloping surface that is on a first side of the partition and that inclines at an angle of inclination with respect to a normal line normal to a corresponding one of the electron incident surfaces, and a second sloping surface that is on a second side of the partition and that inclines at an angle of inclination with respect to the normal line, and
   wherein (i) the angles of inclination of the first sloping surfaces change with positions of the first sloping surfaces along an array direction in which the targets are arrayed, and (ii) the angles of inclination of the second sloping surfaces change with positions of the second slopping surfaces along the array direction, and
   wherein the forward shielding member has a first slope distribution of the first sloping surfaces in the array direction and a second slope distribution of the second sloping surfaces in the array direction, and (i) the first slope distribution showing monotonically increasing or monotonically decreasing of angles of inclination in the array direction and (ii) the second slope distribution showing monotonically increasing or monotonically decreasing of the angles of inclination in the array direction.

2. The X-ray generating unit according to claim 1,
   wherein the forward shielding member has a plurality of apertures each defined by adjacent ones of the partitions; a plurality of X-ray beams are extracted from the respective apertures; and angles formed between the normal lines and center axes of the X-ray beams, respectively, change in the array direction such that the X-ray beams are oriented toward one another and coincide one another, and
   wherein (i) the angles of inclination of the first sloping surfaces change in the array direction and in correspondence with angles of the plurality of X-ray beams and (ii) the angles of inclination of the second sloping surfaces change in the array direction and in correspondence with angles of the plurality of x-ray beams.

3. The X-ray generating unit according to claim 2,
   wherein the forward shielding member faces a detecting plane on which a coinciding area where the plurality of X-ray beams coincide with one another is formed,
   wherein one of the normal lines to the electron incident surfaces that passes through an exposure center, in the array direction, of the coinciding area is defined as a central normal line, and wherein an absolute value of the angle of inclination of each of those sloping surfaces of the partitions that faces the central normal line increases as a distance from the first and second sloping surface to the central normal line is reduced, and an absolute value of the angle of inclination of each of those sloping surfaces of the partitions that stands with its back to the central normal line decreases as a distance from the sloping surface to the central normal line is reduced.

4. The X-ray generating unit according to claim 3, wherein an absolute value of a rate of change, with respect to a position in the array direction, in the angle of inclination of each of those sloping surfaces of the partitions that faces the central normal line decreases as the distance from the sloping surface to the central normal line is reduced; and an absolute value of a rate of change, with respect to the position in the array direction, in the angle of inclination of each of those sloping surfaces of the partitions that stands with its back to the central normal line increases as the distance from the sloping surface to the central normal line is reduced.

5. The X-ray generating unit according to claim 1, wherein each pair of sloping surfaces provided on opposite sides, respectively, of a corresponding one of the center axes incline with respect to the normal line such that virtual planes extended from the pair of sloping surfaces toward a corresponding one of the targets intersect each other between a corresponding one of the electron incident surfaces and the electron source.

6. The X-ray generating unit according to claim 1, wherein the sloping surfaces are provided only in front end portions of the partitions in a height direction.

7. The X-ray generating unit according to claim 1, wherein the forward shielding member includes
a connecting portion that connects the plurality of partitions and extends in the array direction; and
the plurality of apertures defined by the partitions and the connecting portion, and
wherein the apertures are each defined by two or more inclined planes including at least a pair of sloping surfaces.

8. The X-ray generating unit according to claim 1, wherein the each partition contains at least any one of metallic elements, which are lead, gold, platinum, silver, tungsten, molybdenum, tantalum, copper, nickel, and iron.

9. A radiographic apparatus comprising:
the X-ray generating unit according to claim 1; and
an X-ray detecting unit that includes a detecting portion facing the target array and including a plurality of detecting devices.

10. The radiographic apparatus according to claim 9, wherein the X-ray detecting unit further includes a shielding portion provided on an outer side of the detecting portion in the array direction,
wherein the X-ray generating unit forms a main exposed area and an eclipse-attributed penumbra area on the X-ray detecting unit, the eclipse-attributed penumbra area being formed on the outer side of the main exposed area, and
wherein the shielding portion includes at least a part positioned in the eclipse-attributed penumbra area.

11. The radiographic apparatus according to claim 10, wherein the shielding portion includes a part that is positioned on the outer side of the eclipse-attributed penumbra area in the array direction.

12. The radiographic apparatus according to claim 10, wherein the shielding portion is provided on each of two outer sides of the detecting portion in the array direction.

13. The radiographic apparatus according to claim 10, wherein the main exposed area is defined by a main exposed length Lm in the array direction, the main exposed length Lm being expressed as $(n-1) \times p + \{\Phi + (D_{SI}/h_0) \times (\Psi - \Phi)\}$, and the eclipse-attributed penumbra area extends from an edge of the main exposed area in the array direction and toward the outer side in the array direction by an eclipse-attributed penumbra length $w_{min}$ expressed as $\{(D_{SI}-h_0)/h_0\} \times \Phi$, where $h_0$ denotes a height of each of the partitions extending toward a side across the electron incident surfaces from the electron source; $\Phi$ denotes a focal spot diameter of each of focal spots formed on the respective electron incident surfaces by the electron source; p denotes a focal spot pitch; n denotes a number of targets that are arrayed; $\Psi$ denotes an aperture diameter determined by adjacent ones of the partitions; and $D_{SI}$ denotes a source-to-image distance by which the detecting portion is distant from the electron incident surfaces.

14. The radiographic apparatus according to claim 13, wherein the height $h_0$ of the partitions, a width $w_0$ of the shielding portion, and a height $D_0$ of the shielding portion satisfy at least Expressions (1), (2), and (3), respectively, or Expressions (1), (4), and (5), respectively:

[Math. 1]
$$h_0 \leq h_{max} = \frac{p}{p + Li} D_{SI} \tag{1}$$

[Math. 2]
$$w_0 \geq w_{min} = \frac{D_{SI} - h_0}{h_0} \Phi \tag{2}$$

[Math. 3]
$$D_0 < 2\Phi \cdot D_{SI} \cdot \left(\frac{D_{SI} - h_0}{2D_{SI}\Phi + h_0(\Psi - \Phi)}\right) \cdot \left(1 - \frac{w_0}{\Phi} \times \frac{h_0}{D_{SI} - h_0}\right) \tag{3}$$

[Math. 4]
$$w_0 < w_{min} = \frac{D_{SI} - h_0}{h_0} \Phi \tag{4}$$

[Math. 5]
$$D_0 \geq 2\Phi \cdot D_{SI} \cdot \left(\frac{D_{SI} - h_0}{2D_{SI}\Phi + h_0(\Psi - \Phi)}\right) \cdot \left(1 - \frac{w_0}{\Phi} \times \frac{h_0}{D_{SI} - h_0}\right) \tag{5}$$

where Li denotes a length by which X-ray beams emitted from the respective targets coincide with one another on a detecting plane and form the main exposed area.

15. The radiographic apparatus according to claim 14, wherein the height $h_0$ satisfies Expression (6):

[Math. 6]
$$h_0 \geq \frac{1}{10} \frac{p}{p + Li} D_{SI}. \tag{6}$$

16. The radiographic apparatus according to claim 13, wherein the height $h_0$ is 2 mm or larger and 20 mm or smaller.

17. The radiographic apparatus according to claim 9, further comprising:
- a driving circuit connected to the X-ray generating unit and that drives the X-ray generating unit;
- a data processing unit connected to the X-ray detecting unit and that acquires a radiographic image outputted from the X-ray detecting unit; and
- a control unit that controls, via the driving circuit and the data processing unit, the X-ray generating unit and the X-ray detecting unit, respectively, that are in conjunction with each other.

18. The radiographic apparatus according to claim 9, further comprising:
- an object positioning portion provided between the detecting portion and the target array,
- wherein the object positioning portion functions as a breast inserting portion into which a breast of an examinee is to be inserted in a direction intersecting both the array direction and the normal line.

19. The radiographic apparatus according to claim 18, wherein the X-ray generating unit includes a shielding wall extending in the array direction and provided on a side nearer to a body of the examinee than the partitions, the shielding wall having a height $h_2$ that is larger than the height $h_0$ of the partitions.

20. The radiographic apparatus according to claim 19, wherein the height $h_2$ satisfies Expression (7):

[Math. 7]

$$h_2 \geq \frac{D_{SI} \cdot \Phi}{\delta q + \Phi} \tag{7}$$

where $\delta q$ denotes a length of the eclipse-attributed penumbra area in a direction perpendicular to the array direction.

21. The X-ray generating unit according to claim 1, wherein the forward shielding member has a pair of slope angle distributions in the array direction, each of which shows an asymmetrical distribution with respect to a center of the target array.

22. The X-ray generating unit according to claim 1, wherein the forward shielding member has a pair of slope angle distributions in the array direction, each of which shows a stepwise changing depending on a corresponding target position.

* * * * *